United States Patent

Daum et al.

Patent Number: 4,962,104
Date of Patent: Oct. 9, 1990

[54] FUNGICIDAL SUBSTITUTED 2-PHENYL-2,2-DIFLUOROETHYLTHIOL-CARBONATES, COMPOSITIONS AND USE

[75] Inventors: Werner Daum, Krefeld; Dietmar Bielefeldt, Ratingen; Wilhelm Brandes, Leichlingen, all of Fed. Rep. of Germany

[73] Assignee: Bayer Aktiengesellschaft, Leverkusen, Fed. Rep. of Germany

[21] Appl. No.: 446,955

[22] Filed: Dec. 6, 1989

[30] Foreign Application Priority Data

Dec. 17, 1988 [DE] Fed. Rep. of Germany ....... 3842626

[51] Int. Cl.$^5$ .................... A01N 43/10; A01N 43/84; C07D 413/06; C07D 333/38
[52] U.S. Cl. ................... 514/212; 514/231.5; 514/233.5; 514/252; 514/253; 514/324; 514/326; 514/365; 514/422; 514/443; 514/445; 540/546; 544/145; 544/146; 544/376; 544/379; 544/202; 544/213; 548/146; 548/525; 548/527
[58] Field of Search ............... 540/596; 544/145, 146, 544/376, 379; 546/202, 213; 548/146, 525, 527; 549/55, 56, 64; 514/212, 231.5, 233.5, 252, 253, 324, 326, 365, 422, 443, 445

[56] References Cited

FOREIGN PATENT DOCUMENTS 0093384 11/1983 European Pat. Off. .

Primary Examiner—Robert W. Ramsuer
Attorney, Agent, or Firm—Sprung, Horn, Kramer & Woods

[57] ABSTRACT

Fungicidal substituted 2-phenyl-2,2-difluoroethylthiol-carbonates of the formula

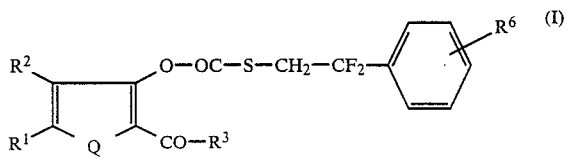

in which
$R^1$ represents hydrogen, alkoxycarbonyl, alkoxyalkoxycarbonyl, alkylthioalkoxycarbonyl, halogenoalkoxycarbonyl, cyanoalkoxycarbonyl, alkenoxycarbonyl, alkynoxycarbonyl and cycloalkyloxycarbonyl, or represents cycloalkylalkoxycarbonyl,
$R^2$ represents hydrogen or alkyl, or represents phenyl, or
$R^1$ and $R^2$ together represent the butadiene-1,4-diyl radical,
$R^3$ represents alkoxy, alkoxyalkoxy, alkylthioalkoxy, fluoroalkoxy, cyanoalkoxy, alkenoxy, alkynoxy, cycloalkyloxy and cycloalkylalkoxy, or represents the group

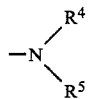

in which
$R^4$ represents alkyl, alkoxyalkyl, alkylthioalkyl, cyanoalkyl, fluoroalkyl, alkenyl, alkinyl or cycloalkyl,
$R^5$ represents hydrogen, alkyl, alkoxyalkyl, alkylthioalkyl, fluoroalkyl, cyanoalkyl, alkenyl, alkinyl or cycloalkyl, or
$R^4$ and $R^5$ together with the nitrogen atom at which they are located represent an unsubstituted or substituted heterocyclic ring which can be substituted in the alkylene chain by further hetero atoms,
$R^6$ represents hydrogen, methyl or chlorine, and
Q represents sulphur or —CH=CH—.

13 Claims, No Drawings

FUNGICIDAL SUBSTITUTED 2-PHENYL-2,2-DIFLUOROETHYLTHIOLCARBONATES, COMPOSITIONS AND USE

The present invention relates to new substituted 2-phenyl-2,2-difluoroethylthiolcarbonates, to processes for their preparation, and to their use for combating pests, in particular fungi.

2-phenyl-2,2-difluoroethylthiolcarbamates which have herbicidal properties have already been disclosed (cf. DE-OS (German Published Specification) No. 3,341,515 and DE-OS (German Published Specification) No. 3,341,516). Furthermore, it has been disclosed that 2,5-bis-(alkoxycarbonyl)-3,4-bis-(acyloxy)-thiophenes and 2,5-bis-(alkoxycarbonyl)-3-alkyl-4-acyloxy-thiophenes possess fungicidal properties (cf. European Patent No. 32,748 and European Patent No. 93,384).

Furthermore, 2,5-bis-(isopropoxycarbonyl)-3-methyl-4-(3-methylbenzoyloxy)-thiophene must be mentioned, which has been disclosed in T. Wada et al., Proceedings of the 10th Intern. Congress of Plant Protection, 20.-25.11.1983, Brighton, Vol. 1, 400–407.

Furthermore, acylthiophene derivatives which have fungicidal properties have been disclosed, such as, for example, 2,5-bis-(isopropoxycarbonyl)-4-methyl-3-(3-trifluoromethylthiobenzoyloxy)-thiophene (cf. DE-OS (German Published Specification) No. 3,402,625).

New substituted 2-phenyl-2,2-difluoroethylthiolcarbonates of the general formula (I)

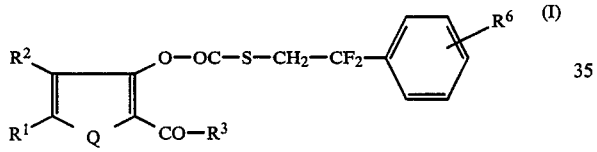

in which
- $R^1$ represents hydrogen, alkoxycarbonyl, alkoxyalkoxycarbonyl, alkylthioalkoxycarbonyl, halogenoalkoxycarbonyl, cyanoalkoxycarbonyl, alkenoxycarbonyl, alkynoxycarbonyl and cycloalkyloxycarbonyl, or represents cycloalkylalkoxycarbonyl,
- $R^2$ represents hydrogen or alkyl, or represents phenyl, or
- $R^1$ and $R^2$ together represent the butadiene-1,4-diyl radical,
- $R^3$ represents alkoxy, alkoxyalkoxy, alkylthioalkoxy, fluoroalkoxy, cyanoalkoxy, alkenoxy, alkynoxy, cycloalkyloxy and cycloalkylalkoxy, or represents the group

in which
- $R^4$ represents alkyl, alkoxyalkyl, alkylthioalkyl, cyanoalkyl, fluoroalkyl, alkenyl, alkinyl or cycloalkyl,
- $R^5$ represents hydrogen, alkyl, alkoxyalkyl, alkylthioalkyl, fluoroalkyl, cyanoalkyl, alkenyl, alkinyl or cycloalkyl or
- $R^4$ and $R^5$ together with the nitrogen atom at which they are located represent an unsubstituted or substituted heterocyclic ring which can be substituted in the alkylene chain by further hetero atoms,
- $R^6$ represents hydrogen, methyl or chlorine, and
- Q represents sulphur or —CH=CH—, have been found.

Furthermore, it has been found that the new 2-phenyl-2,2-difluoroethylthiolcarbonates of the general formula (I)

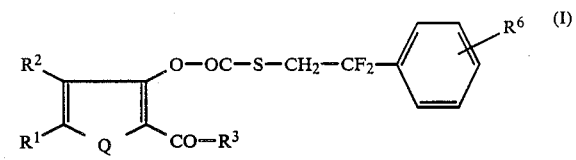

in which
- $R^1$ represents hydrogen, alkoxycarbonyl, alkoxyalkoxycarbonyl, alkylthioalkoxycarbonyl, halogenoalkoxycarbonyl, cyanoalkoxycarbonyl, alkenoxycarbonyl, alkynoxycarbonyl and cycloalkyloxycarbonyl, or represents cycloalkylalkoxycarbonyl,
- $R^2$ represents hydrogen or alkyl, or represents phenyl, or
- $R^1$ or $R^2$ together represent the butadiene-1,4-diyl radical,
- $R^3$ represents alkoxy, alkoxyalkoxy, alkylthioalkoxy, fluoroalkoxy, cyanoalkoxy, alkenoxy, alkynoxy, cycloalkyloxy and cycloalkylalkoxy, or represents the group

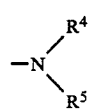

in which
- $R^4$ represents alkyl, alkoxyalkyl, alkylthioalkyl, cyanoalkyl, fluoroalkyl, alkenyl, alkinyl or cycloalkyl,
- $R^5$ represents hydrogen, alkyl, alkoxyalkyl, alkylthioalkyl, fluoroalkyl, cyanoalkyl, alkenyl, alkinyl or cycloalkyl, or
- $R^4$ and $R^5$ together with the nitrogen atom at which they are located represent an unsubstituted or substituted heterocyclic ring which can be substituted in the alkylene chain by further hetero atoms,
- $R^6$ represents hydrogen, methyl or chlorine, and
- Q represents sulphur or —CH=CH—, are obtained when
(a) an aromatic or heteroaromatic hydroxyl compound of the general formula (II)

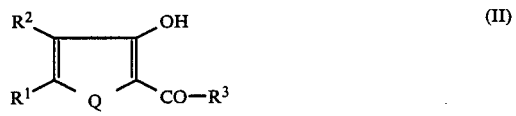

in which
$R^1$, $R^2$, $R^3$ and Q have the abovementioned meaning, or the ammonium, alkali metal or alkaline earth metal salts thereof,
is (are) reacted with an acylating agent of the formula (III)

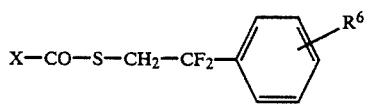 (III)

in which
R⁶ has the abovementioned meaning and
X represents a leaving group, such as, for example, halogen, or by a process in which (b) compounds of the formula (II) are first reacted with phosgene in the presence of a tertiary organic base, and the resulting chlorocarbonyloxy-aromatic compound or chlorocarbonyloxy-heteroaromatic compound of the formula (IV)

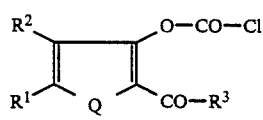 (IV)

in which
R¹, R², R³ and Q have the abovementioned meanings, is then reacted with a 2-phenyl-2,2-difluoroethyl-mercaptan of the formula (V)

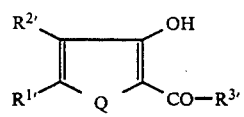 (V)

in which
R⁶ has the abovementioned meaning,
in the presence of an organic or inorganic base and in the presence of solvents and diluents,
or by a process in which (c) in the event that in formula (I)
R² represents alkyl or phenyl,
Q represents sulphur,
R⁶ represents hydrogen, methyl or chlorine and
R¹ and —COR³ are ester groups having different radicals,
a 4-hydroxythiophene derivative of the formula (IIa)

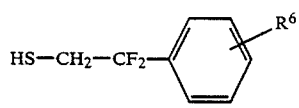 (IIa)

in which
R¹' represents alkoxycarbonyl, alkoxyalkoxycarbonyl, alkylthioalkoxycarbonyl, halogenoalkoxycarbonyl, cyanoalkoxycarbonyl, alkenoxycarbonyl, alkynoxycarbonyl, cycloalkyloxycarbonyl or cycloalkylalkoxycarbonyl,
R²' represents alkyl or phenyl and
R³' represents alkoxy, alkoxyalkoxy, alkylthioalkoxy, fluoroalkoxy, cyanoalkoxy, alkenoxy, alkynoxy, cycloalkyloxy or cycloalkylalkoxy, with the proviso that R¹' and COR³' represent identical ester groups, is partially hydrolyzed in the molar ratio 1:2, using aqueous alcoholic alkali metal hydroxide solution, to give 2-carboxy-4-hydroxy-5-carboxylic acid esters of the formula (IIb)

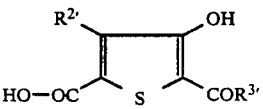 (IIb)

in which
R²' and R³' have the meanings indicated in the case of formula (IIa),
and the compounds of the formula (IIb), after they have been isolated, are reacted with a 2-phenyl-2,2-difluoroethylthiolcarbonyl halide of the formula (III) in the presence of a tertiary organic base to give compounds of the formula (VI)

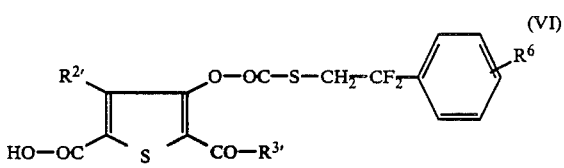 (VI)

in which
R²', R³' and R⁶ have the abovementioned meanings, and the resulting compounds of the formula (VI) are reacted to give acid chlorides of the formula (VII)

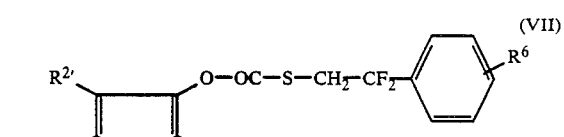 (VII)

in which
R²', R³' and R⁶ have the abovementioned meanings, and, in a last step, these compounds are esterified with an alcohol of the formula (VIII)

R¹"OH    (VIII)

in which
R¹" represents alkyl, alkoxyalkyl, alkylthioalkyl, halogenoalkyl, cyanoalkyl, alkenyl, alkinyl, cycloalkyl or cycloalkylalkyl,
in the presence of an organic base.

Furthermore, it has been found that the new substituted 2-phenyl-2,2-difluoroethylthiolcarbonates of the formula (I) show powerful effects against pests, in particular against fungi.

Surprisingly, the substituted 2-phenyl-2,2-difluoroethylthiolcarbonates of the formula (I) according to the invention show a better activity against phytopathogenic fungi than the compounds of a similar structure and the same direction of action which are known from the prior art, while showing outstanding tolerance by plants.

Formula (I) provides a general definition of the substituted 2-phenyl-2,2-difluoroethylthiolcarbonates according to the invention. Preferred compounds of the formula (I) are those in which
R¹ represents hydrogen, or represents alkoxycarbonyl having 1–7 carbon atoms, or represents alkoxyalkoxycarbonyl or represents alkylthioalkoxycarbonyl, in each case having 1–5 carbon atoms per alkyl moiety, or represents halogenoalkoxycarbonyl having 1–5 carbon atoms and 1–5 identical or different halogen atoms, or represents cyanoalkoxycarbonyl having 1–5 carbon atoms in the alkyl moiety, or represents alkenoxycarbonyl having 3 or 4 carbon atoms in the alkene moiety, or represents alkynoxycarbonyl having 3–5 carbon atoms in the alkyne moiety, or represents cycloalkyloxycarbonyl having 4–6 carbon atoms in the cycloalkyl moiety, or cycloalkylalkoxycarbonyl having 4–8 carbon atoms in the cycloalkylalkoxy moiety, $R^2$ represents hydrogen, or represents alkyl having 1–4 carbon atoms or represents phenyl, or $R^1$ and $R^2$ together represent the butadiene-1,4-diyl radical, $R^3$ represents alkoxy having 1–6 carbon atoms, or represents alkoxyalkoxy or represents alkylthioalkoxy, each having 1–5 carbon atoms per alkyl moiety, or represents fluoroalkoxy having 1–5 carbon atoms and 1–5 fluorine atoms, or represents cyanoalkoxy having 1–5 carbon atoms in the alkyl moiety, or represents alkenoxy having 3 or 4 carbon atoms, or represents alkynoxy having 3–5 carbon atoms, or represents cycloalkyloxy having 4–6 carbon atoms or represents cycloalkylalkoxy having 4–8 carbon atoms or represents the group

in which $R^4$ represents alkyl having 1–5 carbon atoms, or represents alkoxyalkyl or alkylthioalkyl, each having 1–5 carbon atoms per alkyl moiety, or represents cyanoalkyl having 1–5 carbon atoms in the alkyl moiety, or represents fluoroalkyl having 1–3 fluorine atoms and 1–5 carbon atoms, or represents alkenyl or alkinyl, each having 3–5 carbon atoms, or cycloalkyl having 3–6 carbon atoms, $R^5$ represents hydrogen or alkyl having 1–5 carbon atoms, or represents alkoxyalkyl or alkylthioalkyl, in each case having 1–5 carbon atoms per alkyl moiety, or represents cyanoalkyl having 1–5 carbon atoms in the alkyl moiety, or represents fluoroalkyl having 1–3 fluorine atoms and 1–5 carbon atoms, or represents alkenyl or alkinyl having 3–5 carbon atoms, or cyclohexyl, or $R^4$ and $R^5$ together with the nitrogen atom at which they are located represent a 5-, 6- or 7-membered heterocyclic ring which can contain a further 1 to 3 identical or different hetero atoms—such as aza, oxa or thia elements—and which can be monosubstituted to trisubstituted by identical or different alkyl groups having 1–4 carbon atoms, $R^6$ represents hydrogen, methyl or chlorine and Q represents sulphur or represents —CH=CH—.

Particularly preferred compounds of the formula (I) are those in which $R^1$ represents hydrogen, methoxycarbonyl, ethoxycarbonyl, n- or isopropoxycarbonyl, 2,2-dimethylpropoxycarbonyl, 2-methoxyethoxycarbonyl, 2-ethoxyethoxycarbonyl, 2-methylthioethoxycarbonyl, 2-ethylthioethoxycarbonyl, 2,2,2-trifluoroethoxycarbonyl, cyanomethoxycarbonyl, cyanoethoxycarbonyl, allyloxycarbonyl, methallyloxycarbonyl, 2-propynyloxycarbonyl, 1,1-dimethyl-2-propynyloxycarbonyl, cyclopentyloxycarbonyl, cyclohexyloxycarbonyl or cyclohexylmethoxycarbonyl, $R^2$ represents hydrogen, methyl, ethyl, n-propyl, iso-propyl, n-butyl, sec.-butyl, iso-butyl, tert.butyl or phenyl, or $R^1$ and $R^2$ together represent the butadiene-1,4-diyl radical, $R^3$ represents methoxy-, ethoxy-, n- or isopropoxy-, sec.-butoxy-, 2,2-dimethylpropoxy-, 2-methoxyethoxy-, 2-ethoxyethoxy-, 2-methylthioethoxy-, 2-ethylthioethoxy-, 2,2,2-trifluoroethoxy-, cyanomethoxy-, cyanoethoxy-, allyloxy-, methallyloxy-, 2-propynyloxy-, 1,1-dimethyl-2-propynyloxy-, cyclopentyloxy-, cyclohexyloxy- or cyclohexylmethoxy-, or represents the group

in which $R^4$ represents methyl, ethyl, n- or iso-propyl, 2,2-dimethylpropyl, 2-methoxyethyl, 2-ethoxyethyl, 2-propoxyethyl, 3-methoxypropyl, 3-ethoxypropyl, 3-butoxypropyo, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propynyl, 1,1-dimethyl-2-propynyl, cyclopropyl, cyclobutyl, cyclopentyl or cyclohexyl, $R^5$ represents hydrogen, methyl, ethyl, n- or isopropyl, 2,2-dimethylpropyl, 2-methoxyethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propynyl, 1,1-dimethyl-2-propynyl or cyclohexyl, or $R^4$ and $R^5$ together with the nitrogen atom at which they are located represent pyrrolidine, piperidine, 2-methylpiperidine, 3-methylpiperidine, 4-methylpiperidine, hexahydro-1H-azepine, morpholine, 2,6-dimethylmorpholine, thiazolidine, $N^1$-methylpiperazine or $N^1$-propylpiperazine, $R^6$ represents hydrogen, methyl or chlorine and Q represents sulphur, or represents —CH=CH—.

Compounds of the formula (I) which may very particularly preferably be mentioned are those in which $R^1$ represents hydrogen, ethoxycarbonyl, isopropoxycarbonyl, sec.-butoxycarbonyl or cyclopentyloxycarbonyl, $R^2$ represents hydrogen, methyl, isopropyl or phenyl, $R^3$ represents ethoxy, isopropoxy, sec.-butoxy or cyclopentyloxy, or represents the group

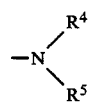

in which $R^4$ represents methyl or methoxyethyl and $R^5$ represents hydrogen, or $R^4$ and $R^5$ together represent pentane-1,5-diyl, or represent 3-oxa-pentane-1,5-diyl, $R^6$ represents hydrogen, methyl or chlorine and Q represents sulphur, or represents —CH=CH—.

Furthermore, there are mentioned compounds of the formula (I) in which $R^1$ and $R^2$ together represent the butadiene-1,4-diyl radical, $R^3$ represents ethoxy, isopropoxy, sec.-butoxy or cyclopentyloxy, or represents the group

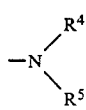

in which $R^4$ represents methyl or methoxyethyl, $R^5$ represents hydrogen or methyl, or $R^4$ and $R^5$ together represent pentane-1,5-diyl, or represent 3-oxa-pentane-1,5-diyl, $R^6$ represents hydrogen, methyl or chlorine, and Q represents sulphur, or represents —CH=CH—.

In addition, there are mentioned in particular compounds of the formula (I) in which $R^1$ represents hydrogen, ethoxycarbonyl, isopropoxycarbonyl, sec.-butoxycarbonyl or cyclopentyloxycarbonyl, $R^2$ represents hydrogen, methyl, isopropyl or phenyl, $R^3$ represents ethoxy, isopropoxy, sec.-butoxy or cyclopentyloxy, $R^6$ represents hydrogen or methyl, and Q represents —CH=CH—.

Other compounds of the formula (I) which may be mentioned in particular are those in which $R^1$ represents hydrogen, ethoxycarbonyl, isopropoxycarbonyl, sec.-butoxycarbonyl or cyclopentyloxycarbonyl, $R^2$ represents hydrogen, methyl, isopropyl or phenyl, $R^3$ represents ethoxy, isopropoxy, sec.-butoxy or cyclopentyloxy, $R^6$ represents hydrogen or methyl and Q represents sulphur.

In the case of the substituents $R^{1'}$, $R^{1''}$, $R^{2'}$ and $R^{3'}$, the respective parts of $R^1$, $R^2$ and $R^3$ are true for the preferred, particularly preferred and especially preferred definitions.

The alkyl radicals as such or in combinations, such as alkoxy, alkylthioalkoxy, cyanoalkyl and the like, can in each case be straight-chain or branched.

If the aromatic and/or hetero-aromatic radicals are substituted, this is taken to mean that they are monosubstituted to pentasubstituted, preferably mono substituted to trisubstituted, by identical or different substituents, unless stated otherwise.

If 2,5-bis-(cyclopentyloxycarbonyl)-3-phenyl-4-hydroxythiophene and 2,2-difluoro-2-(4-chlorophenyl)-ethylthiolcarbonyl fluoride are used as starting substances for the preparation of the compounds of the formula (I) according to the invention by process variant (a), and pyridine is used as the solvent and as the hydrogen fluoride acceptor, the course of the reaction can be represented by the following equation:

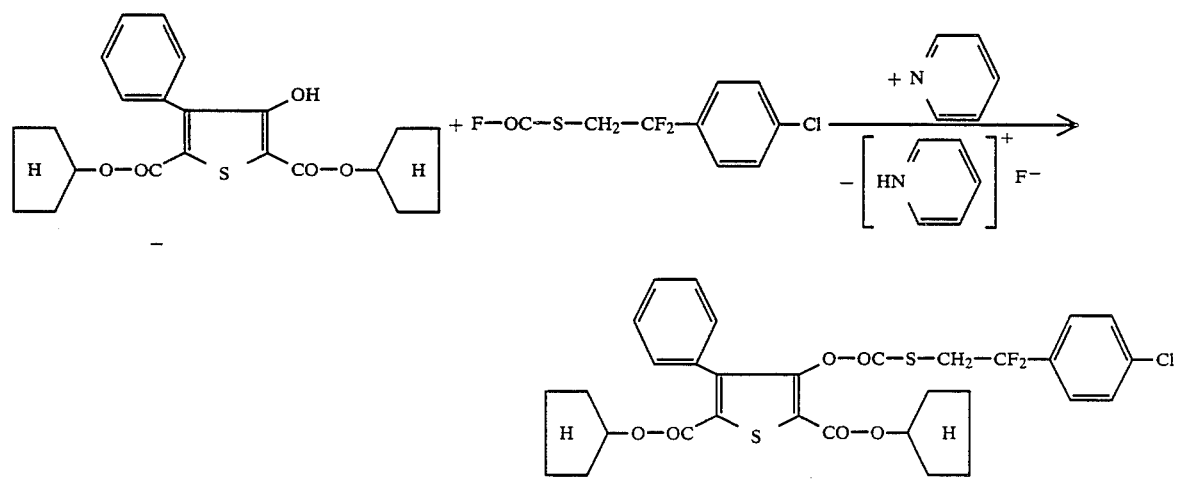

If, for example, 2,5-bis-(cyclopentyloxycarbonyl)-3-phenyl-4-hydroxythiophene and phosgene are used in a 1st step and 2-phenyl-2,2-difluoroethylmercaptan in a 2nd step as starting substances for the preparation of the compounds of the formula (I) according to the invention by process variant (b), the course of the reaction can be represented by the following equation:

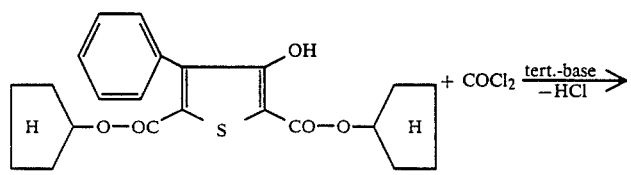

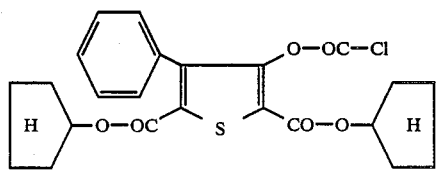

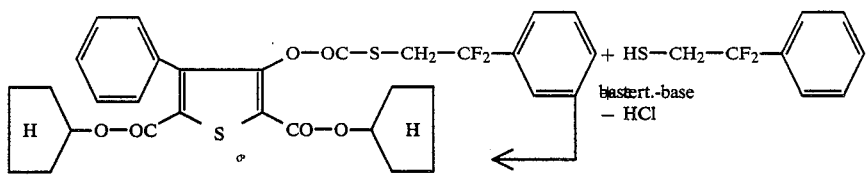

If, for example, 2,5-bis-(i-propyloxycarbonyl)-3-phenyl-4-hydroxythiophene and aqueous alcoholic alkali metal hydroxide solution are used in a 1st step as starting substances for the preparation of compounds of the formula (I) according to the invention by process variant (c), and if then in a 2nd step a reaction is carried out with 2-phenyl-2,2-difluoroethylthiolcarbonyl chloride and subsequently with, for example, oxalyl chloride in dimethylformamide in the presence of an organic base, and subsequently with sec.-butanol in the presence of an organic base, the course of the reaction can be represented by the following equation:

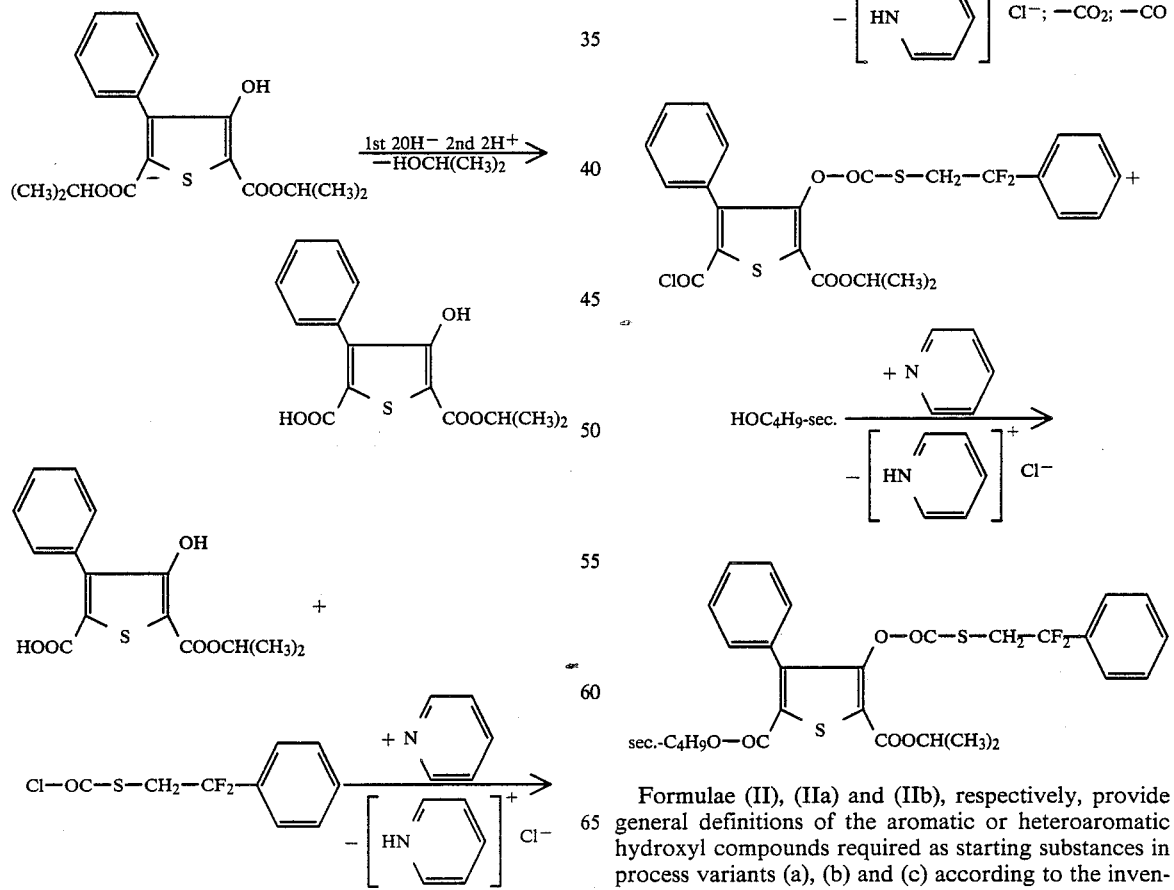

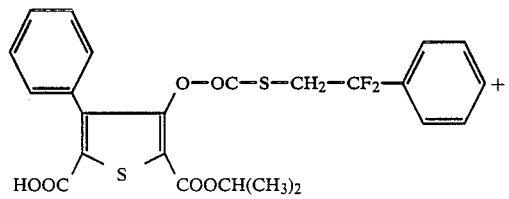

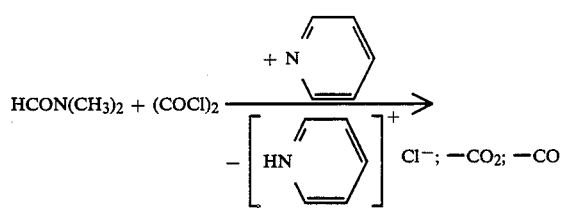

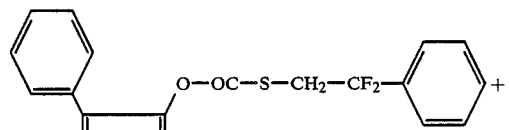

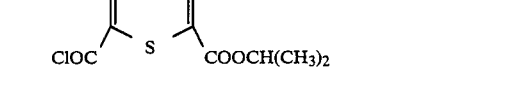

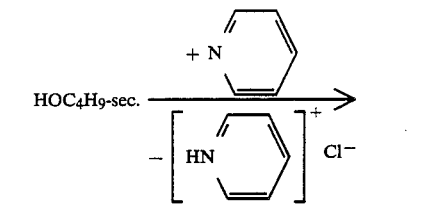

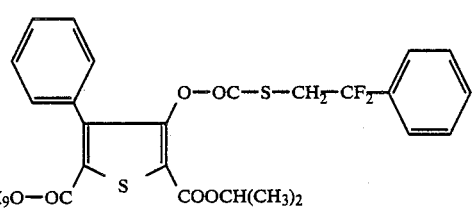

Formulae (II), (IIa) and (IIb), respectively, provide general definitions of the aromatic or heteroaromatic hydroxyl compounds required as starting substances in process variants (a), (b) and (c) according to the invention. The majority of the compounds are known, and can be prepared by known processes. In particular, the following may be mentioned here:

isopropyl salicylate, sec.-butyl salicylate and cyclopentyl salicylate, and N-salicylyl-pyrrolidine;

2-ethyl 1-hydroxynaphthoate, isopropyl 1-hydroxynaphthoate, n-propyl 1-hydroxynaphthoate and cyclopentyl 1-hydroxynaphthoate, and N-1-hydroxynaphthoyl 2-morpholine, -piperidine and -pyrrolidine; methyl 3-hydroxythiophene-2-carboxylate, ethyl 3-hydroxythiophene-2-carboxylate, isopropyl 3-hydroxythiophene-2-carboxylate and sec.-butyl 3-hydroxythiophene-2-carboxylate;

2,5-bis-(methoxycarbonyl)-, 2,5-bis-(ethoxycarbonyl)-, 2,5-bis-(isopropoxycarbonyl)-, 2,5-bis-(butyloxycarbonyl)- and 2,5-bis-(sec.-butyloxycarbonyl)-3-hydroxythiophene;

2,5-bis-(methoxycarbonyl)-, 2,5-bis-(ethoxycarbonyl)-, 2,5-bis-(isopropoxycarbonyl)-, 2,5-bis-(propoxycarbonyl)-, 2,5-bis-(sec.-butoxycarbonyl)-, 2,5-bis-(isobutoxycarbonyl)-, 2,5-bis-(pentoxycarbonyl)-, 2,5-bis-(cyclopentyloxycarbonyl)- and 2,5-bis-(cyclohexylmethoxycarbonyl)-3-methyl-, -3-isopropyl- and -3-phenyl-4-hydroxythiophene;

N-methyl-2-methoxycarbonyl-3-methyl-4-hydroxythiophene-5-carboxamide;

N-methyl-, N,N-dimethyl-, N,(2-methoxyethyl)- and N-(3-methoxypropyl)-2-ethoxycarbonyl-3-methyl-4-hydroxythiophene-5-carboxamide, and N-2-ethoxycarbonyl-3-methyl-4-hydroxythiophene-5-carboxyl-pyrrrolidine, -piperidine and -morpholine;

N-methyl-, N,N-dimethyl-, N-(2-methoxyethyl)-, N-(3-methoxypropyl)-, N-(2-ethoxyethyl)- and N-tert.-butyl-2-isopropoxycarbonyl-3-methyl-4-hydroxythiophene-5-carboxamide, and N-2-isopropoxycarbonyl-3-methyl-4-hydroxythiophene-5-carboxyl-pyrrolidine,-piperidine and morpholine;

N-2-propoxycarbonyl-3-methyl-4-hydroxythiophene-5-carboxyl-morpholine and-piperidine;

N-(2-methoxyethyl)- and N-(3-methoxypropyl)-2-butoxycarbonyl-3-methyl-4-hydroxy-thiophene-5-carboxamide;

N-(2-methoxyethyl)-, N-(2-ethoxyethyl)- and N-(3-methoxypropyl)-2-sec.-butoxycarbonyl-3-methyl-4-hydroxythiophene-5-carboxamide, and N-2-sec.-butoxycarbonyl-3-methyl-4-hydroxythiophene-5-carboxyl-morpholine, -piperidine and -pyrrolidine;

N-2-isobutoxycarbonyl-3-methyl-4-hydroxythiophene-5-carboxyl-morpholine and -piperidine;

N-(2-methoxyethyl)-2-cyclopentyloxycarbonyl-3-methyl-4-hydroxythiophene-5-carboxamide, and N-2-cyclopentyloxycarbonyl-3-methyl-4-hydroxythiophene-5-carboxyl-morpholine and -piperidine;

N-2-ethoxycarbonyl-3-isopropyl-4-hydroxythiophene-5-carboxyl-morpholine, -piperidine and -pyrrolidine;

N-(2-methoxyethyl)-2-isopropoxycarbonyl-3-isopropyl-4-hydroxythiophene-5-carboxamide, and N-2-isopropoxy-carbonyl-3-isopropyl-4-hydroxythiophene-5-carboxylmorpholine, -piperidine and -pyrrolidine;

N-(2-methoxyethyl)-2-n-propoxycarbonyl-3-isopropyl-4-hydroxythiophene-5-carboxamide, and N-2-n-propoxycarbonyl-3-isopropyl-4-hydroxythiophene-5-morpholine and -piperidine;

N-2-methoxycarbonyl-3-phenyl-4-hydroxythiophene-5-carboxyl-morpholine and -piperidine;

N-methyl-, N,N-dimethyl-, N-(2-methoxyethyl)-, N-(2-ethoxyethyl)- and N-(3-methoxypropyl)-2-ethoxy-, -2-isopropoxy-, -2-propoxy-, -2-sec.-butoxy-, -2-isobutoxy- and -2-cyclopentyloxy-carbonyl-3-phenyl-4-hydroxythiophene-5-carboxamide, and N-2-ethoxy-, N-2-isopropoxy-, N-2-propoxy-, N-2-sec.-butoxy-, N-2-isobutoxy- and N-2-cyclopentyloxy-carbonyl-3-phenyl-4-hydroxythiophene-5-carboxyl-morpholine, -piperidine and -pyrrolidine.

Hydroxythiophenecarboxylic acid derivatives are disclosed in, for example, DE-OS (German Published Specification) Nos. 3,523,313 and 3,602,889, Ber. 89, 1897 (1936), Indian J. of Chem. 11, 313–314 (1973) and European Patent Specification No. 93,384.

Phosgene, which is required in process variant (b), is a known substance which is produced on a large scale, as are the alcohols of the formula (VIII) mentioned in process variant (c).

Other compounds which are required in process variants (a) and (c) for the reactions to give the compounds of the formula (I) according to the invention are 2-phenyl-2,2-difluoroethylthiolcarbonyl halides, for which formula (III) provides a general definition. The preparation of these compounds is disclosed in DE-OS (German Published Specifications) Nos. 3,341,515 and 3,341,516.

Suitable diluents for the reaction according to the invention of an aromatic or heteroaromatic hydroxycarboxylic acid derivative of the formulae (II) and (IIa), respectively, with an acylating agent of the formula (III) by process variants (a) and (c) are all organic solvents which are inert towards the reactants; polar solvents are preferably used. Examples which may be mentioned in this context are acetonitrile, acetone, chloroform, benzonitrile, dimethylacetamide, dimethylformamide, dimethyl sulphoxide, chlorobenzene, ethyl acetate, dioxane, methyl ethyl ketone, methylene chloride and tetrahydrofuran.

Acid binders which are used for the reaction are organic bases, preferably tertiary amines. The following may be mentioned in this context: quinoline, dimethylbenzylamine, dimethylaniline, ethyldicyclohexylamine, ethyldiisopropylamine, picoline, pyridine and triethylamine.

It is also possible to use an excess of tertiary amine simultaneously as the solvent. For carrying out the process according to the invention, it is also possible to initially introduce alkali metal salts or alkaline earth metal salts of the aromatic or heteroaromatic hydroxycarboxylic acid derivatives to be reacted in an inert solvent, or the salt is prepared by transferring alkali metal hydroxide solution, alkoxides or a corresponding alkaline earth metal compound into a mixture of the aromatic or heteroaromatic hydroxycarboxylic acid derivative, and then carefully removing the water, or distilling off the alcohol, or adding an alkali metal hydride or alkaline earth metal hydride. It may also be advantageous to carry out the reaction in the presence of a catalyst, such as, for example, 4-dimethylaminopyridine.

It is also possible to carry out the reactions in heterogeneous systems consisting of water and a waterimmiscible solvent.

The reaction temperatures and the duration of the reaction are determined by the activity of the starting materials. In general, the process is carried out between about −50° and about +80° C., preferably between −10° and 60° C.

For reacting an aromatic or heteroaromatic hydroxycarboxylic acid derivative of the formula (II) first with phosgene and subsequently with a mercaptan of the formula (V) by process (b), a mixture consisting of an aromatic or heteroaromatic hydroxycarboxylic acid derivative of the formula (II), a tertiary amine, such as, for example, quinoline, dimethylbenzylamine, dimethylaniline, ethyldicyclohexylamine, ethyldiisopropylamine, picoline, pyridine or triethylamine, and an inert organic solvent, such as, for example, methylene chloride, chloroform, chlorobenzene, ethyl acetate, toluene or xylene, is added in a first step to excess phosgene, dissolved in the inert organic solvent. This process is generally carried out between −50° and +80° C., preferably at 0° to +30° C.

After the 4-chlorocarbonyloxy derivative of the formula (IV) has been isolated, it is reacted with a mercaptan of the formula (V) in the presence of an organic or inorganic base, or with a salt of the mercaptan of the formula (V).

Suitable solvents for this reaction are, in principle, solvents which are miscible or not miscible with water, as listed above. In general, the process is carried out at temperatures corresponding to those of the phosgenation reaction.

In formula (III), the leaving group X is preferably halogen. The compounds of the formulae (IV), (V), (VI) and (VII) are either known or can be prepared analogously by known processes.

In process variant (c), acid chlorides, such as, for example, oxalyl chloride, are used for the preparation of the carbonyl chlorides.

Depending on the reaction conditions, the active compounds according to the invention either precipitate as crystals, or they remain dissolved in the organic water, can then be precipitated by carefully concentrating the solution or by the addition of weakly polar organic solvents, such as cyclohexane, dibutyl ether, diisopropyl ether or carbon tetrachloride. If necessary, water-miscible, polar solvents have to be removed after the reaction by evaporating in vacuo.

If the compounds according to the invention are dissolved in a water-miscible solvent, they can also be precipitated by the addition of water.

Some of the compounds according to the invention decompose at a higher temperature; in these cases, the melting points can only be determined at a low level of accuracy, or not at all. The presence of certain structural elements can be seen from the NMR spectra.

The active compounds according to the invention show a powerful biological action and can be employed in practice for combating pests. The active compounds are therefore suitable, inter alia, for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Pythium species, such as, for example, *Pythium ultimum;* Phytophthora species, such as, for example, *Phytophthora infestans;*

Pseudoperonospora species, such as, for example, *Pseudoperonospora humuli* or *Pseudoperonospora cubensis;* Plasmopara species, such as, for example, *Plasmopara viticola;*

Peronospora species, such as, for example, *Peronospora pisi* or *P. brassicae;*

Erysiphe species, such as, for example, *Erysiphe graminis;*

Spaerotheca species, such as, for example, *Sphaerotheca fuliginea;*

Podosphaera species, such as, for example, *Posophaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospho-lipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound preparation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The compounds of the formula (I) according to the invention have a particularly good action against fungal pests in fruit growing and vegetable growing, and the action against pests in rice growing may also be mentioned.

PREPARATION EXAMPLES

Example 1

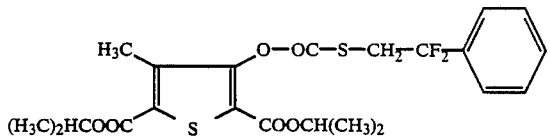

14 g of 2,5-bis-(isopropoxycarbonyl)-3-methyl-4-hydroxythiophene (0.049 mol) and 0.02 g of 4-dimethylaminopyridine are initially introduced into 100 ml of dry pyridine at 20° C. 12 g of 2-phenyl-2,2-difluoroethylthiolcarbonyl fluoride (0.054 mol) are added dropwise, and the reaction mixture is then maintained at 60° C for 4 hours. 250 ml of ethyl acetate are added, the mixture is washed once with ice-cold water, once with dilute sodium carbonate solution and once with water, and dried over sodium sulphate. The reaction solution is evaporated under a waterpump vacuum. The evaporation residue is chromatographed on silica gel 60 using methyl cyclohexane/toluene/acetic acid in a ratio by volume of 3/5/1. The product fraction is evaporated, and the evaporation residue is dried at 60° C./0.1 mbar. 17 g of 2,5-bis-(isopropoxycarbonyl)-3-methyl-4-(2-phenyl-2,2-difluoroethylthiocarbonyloxy)-thiophene are obtained as a viscous composition.

$^1$H—NMR (CDCl$_3$): COOCH 5.20 (m, 2H); CH$_3$ 2.26 (s, 3H); S—CH$_2$—CF$_2$ 3.71 (t, 2H).

The compound crystallizes from petroleum ether, m.p. 66.5° C.

The compounds of the formula (I) of Examples 2 to 9 are obtained in the same manner as indicated in Example 1 or in the description:

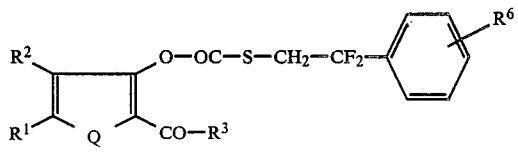

(I)

| Example No. | $R^1$ | $R^2$ | $R^3$ | $R^6$ | Q | Physical data |
|---|---|---|---|---|---|---|
| 2 | —COOC$_2$H$_5$ | CH$_3$ | —N(morpholine) | H | S | m.p.: 68° C. |
| 3 | —COOC$_3$H$_7$-n | C$_6$H$_5$ | —N(piperidine) | H | S | *$^1$H-NMR (CDCl$_3$): COOCH$_2$ 4.07 (t,2H); CON(CH$_2$CH$_2$) + SCH$_2$CF$_2$ 3.35–3.65 (m;6H) |
| 4 | —COOC$_2$H$_5$ | C$_6$H$_5$ | —OC$_2$H$_5$ | H | S | m.p.: 121° C. |
| 5 | H | H | —OCH(CH$_3$)$_2$ | H | —CH=CH— | *$^1$H-NMR (CDCl$_3$): COOCH 5.22 (m,1H); SCH$_2$CF$_2$ 3.69 (t,2H) |
| 6 | —COOCH(CH$_3$)$_2$ | CH(CH$_3$)$_2$ | —OCH(CH$_3$)$_2$ | H | S | *$^1$H-NMR (CDCl$_3$): COOCH 5.18 (m,2H); SCH$_2$CF$_2$ 3.7 (m,2H) |
| 7 | —COOCH(CH$_3$)$_2$ | CH$_3$ | —N(morpholine) | H | S | $^1$H-NMR (CDCl$_3$): COOCH 5.20 (m,1H); N—CH$_2$—CH$_2$—O + SCH$_2$CF$_2$ 3,4–3,8 (m,10H) |
| 8 | —COOCH(CH$_3$)$_2$ | C$_6$H$_5$ | —OCH(CH$_3$)$_2$ | H | S | *$^1$H-NMR (CDCl$_3$): COOCH 5.06 + 5.22 (2m,2H); SCH$_2$CF$_2$ 3.58 (t,2H) |
| 9 | —COOCH(CH$_3$)$_2$ | CH$_3$ | —N(piperidine) | H | S | *$^1$H-NMR (CDCl$_3$): COOCH 5.19 (m,1H); SCH$_2$CF$_2$ 3.66 (t,2H) |
| 10 | H | H | —OCH(CH$_3$)$_2$ | H | S | *$^1$H-NMR (CDCl$_3$): COOCH 5.18 (m,1H); SCH$_2$CF$_2$ 3.70 (t,2H) |
| 11 | —COOC$_2$H$_5$— | CH$_3$ | —OC$_2$H$_5$ | H | S | *$^1$H-NMR (CDCl$_3$): COOCH$_2$ 4.34 (m,4H); SCH$_2$CF$_2$ 3.70 (t,2H) |
| 12 | —COOCH(CH$_3$)C$_2$H$_5$ | CH$_3$ | —OCH(CH$_3$)C$_2$H$_5$ | H | S | *$^1$H-NMR (CDCl$_3$): COOCH 5.04 (m,2H); SCH$_2$CF$_2$ 3.71 (t,2H) |
| 13 | —COO-cyclopentyl | CH$_3$ | —O-cyclopentyl | H | S | m.p.: 95.5° C. |
| 14 | —COOCH(CH$_3$)$_2$ | CH$_3$ | —OCH(CH$_3$)$_2$ | CH$_3$ | S | *$^1$H-NMR (CDCl$_3$): COOCH 5.21 (m,2H); SCH$_2$CF$_2$ 3.69 (t,2H); ar-CH$_3$ 2.39 (s,3H); hetar-CH$_3$ 2.28 (s,3H) |

*viscous product

USE EXAMPLES

In the Use Examples which follow, the compounds listed below are employed as comparison substances:

65

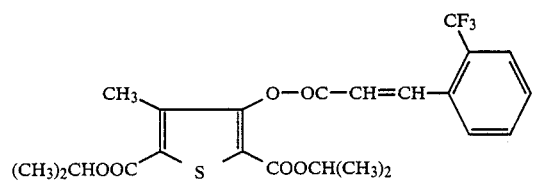

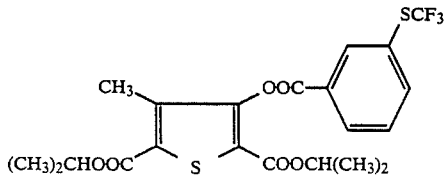

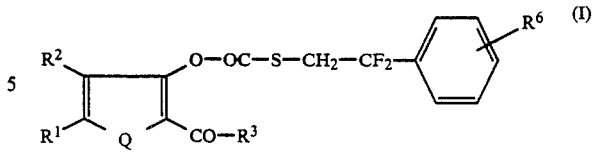

disclosed in DE No. 3,402,625.

EXAMPLE A

Podosphaera test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Podosphaera leucotricha*.

The plants are then placed in a greenhouse at 23° C. and at a relative atmospheric humidity of about 70%.

Evaluation is carried out 9 days after the inoculation.

In this test, a clearly superior activity compared with the prior art is shown, for example, by the compounds according to the Preparation Examples 1 and 3.

EXAMPLE B

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23 to 24° C. and at a relative atmospheric humidity of about 75%.

Evaluation is carried out 10 days after the inoculation.

In this test, a clearly superior activity compared with the prior art is shown, for example, by the compounds according to the Preparation Examples 1 and 3.

It is understood that the specification and examples are illustrative but not limitative of the present invention and that other embodiments within the spirit and scope of the invention will suggest themselves to those skilled in the art.

We claim:

1. A substituted 2-phenyl-2,2-difluoroethylthiolcarbonate of the formula in which $R^1$ represents hydrogen, alkoxycarbonyl, alkoxyalkoxycarbonyl, alkylthioalkoxycarbonyl, halogenoalkoxycarbonyl, cyanoalkoxycarbonyl, alkenoxycarbonyl, alkynoxycarbonyl and cycloalkyloxycarbonyl, or represents cycloalkylalkoxycarbonyl, $R^2$ represents hydrogen or alkyl, or represents phenyl, or $R^1$ and $R^2$ together represent the butadiene-1,4-diyl radical, $R^3$ represents alkoxy, alkoxyalkoxy, alkylthioalkoxy, fluoroalkoxy, cyanoalkoxy, alkenoxy, alkynoxy, cycloalkyloxy and cycloalkylalkoxy, or represents the group

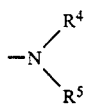

in which $R^4$ represents alkyl, alkoxyalkyl, alkylthioalkyl, cyanoalkyl, fluoroalkyl, alkenyl, alkinyl or cycloalkyl, $R^5$ represents hydrogen, alkyl, alkoxyalkyl, alkylthioalkyl, fluoroalkyl, cyanoalkyl, alkenyl, alkinyl or cycloalkyl, or $R^4$ and $R^5$ together with the nitrogen atom at which they are located represent an unsubstituted or substituted heterocyclic ring which can be substituted in the alkylene chain by further hetero atoms, $R^6$ represents hydrogen, methyl or chlorine, and Q represents sulphur.

2. A substituted 2-phenyl-2,2-difluoroethylthiolcarbonate according to claim 1, in which $R^1$ represents hydrogen, or represents alkoxycarbonyl having 1–7 carbon atoms, or represents alkoxyalkoxycarbonyl or represents alkylthioalkoxycarbonyl, in each case having 1–5 carbon atoms per alkyl moiety, or represents halogenoalkoxycarbonyl having 1–5 carbon atoms and 1–5 identical or different halogen atoms, or represents cyanoalkoxycarbonyl having 1–5 carbon atoms in the alkyl moiety, or represents alkenoxycarbonyl having 3 or 4 carbon atoms in the alkene moiety, or represents alkynoxycarbonyl having 3–5 carbon atoms in the alkyne moiety, or represents cycloalkyloxycarbonyl having 4–6 carbon atoms in the cycloalkyl moiety, or cycloalkylalkoxycarbonyl having 4–8 carbon atoms in the cycloalkylalkoxy moiety, $R^2$ represents hydrogen, or represents alkyl having 1–4 carbon atoms or represents phenyl, or $R^1$ and $R^2$ together represent the butadiene-1,4-diyl radical, $R^3$ represents alkoxy having 1–6 carbon atoms, or represents alkoxyalkoxy or represents alkylthioalkoxy, each having 1–5 carbon atoms per alkyl moiety, or represents fluoroalkoxy having 1–5 carbon atoms and 1–5 fluorine atoms, or represents cyanoalkoxy having 1–5 carbon atoms in the alkyl moiety, or represents alkenoxy having 3 or 4 carbon atoms, or represents alkynoxy having 3–5 carbon atoms, or represents cycloalkyloxy having 4–6 carbon atoms or represents cycloalkylalkoxy having 4–8 carbon atoms or represents the group

in which

R$^4$ represents alkyl having 1–5 carbon atoms, or represents alkoxyalkyl or alkylthioalkyl, each having 1–5 carbon atoms per alkyl moiety, or represents cyanoalkyl having 1–5 carbon atoms in the alkyl moiety, or represents fluoroalkyl having 1–3 fluorine atoms and 1–5 carbon atoms, or represents alkenyl or alkinyl, each having 3–5 carbon atoms, or cycloalkyl having 3–6 carbon atoms, R$^5$ represents hydrogen or alkyl having 1–5 carbon ( atoms, or represents alkoxyalkyl or alkylthioalkyl, in each case having 1–5 carbon atoms per alkyl moiety, or represents cyanoalkyl having 1–5 carbon atoms in the alkyl moiety, or represents fluoroalkyl having 1–3 fluorine atoms and 1–5 carbon atoms, or represents alkenyl or alkinyl having 3–5 carbon atoms, or cyclohexyl, or R$^4$ and R$^5$ together with the nitrogen atom at which they are located represent a 5-, 6- or 7-membered heterocyclic ring which can contains 1 to 3 a further identical or different aza, oxa or thia elements and which can be monosubstituted to trisubstituted by identical or different alkyl groups having 1–4 carbon atoms, R$^6$ represents hydrogen, methyl or chlorine and Q represents sulphur.

3. A substituted 2-phenyl-2,2-difluoroethylthiolcarbonate according to claim 1, in which R$^1$ represents hydrogen, methoxycarbonyl, ethoxycarbonyl, n- or isopropoxycarbonyl, 2,2-dimethylpropoxycarbonyl, 2-methoxyethoxycarbonyl, 2-ethoxyethoxycarbonyl, 2-methylthioethoxycarbonyl 2-ethylthioethoxycarbonyl, 2,2,2-trifluoroethoxycarbonyl, cyanomethoxycarbonyl, cyanoethoxycarbonyl, allyloxycarbonyl, methallyloxycarbonyl, 2-propynyloxycarbonyl, 1,1-dimethyl-2-propynyloxycarbonyl, cyclopentyloxycarbonyl, cyclohexyloxycarbonyl or cyclohexylmethoxycarbonyl, R$^2$ represents hydrogen, methyl, ethyl, n-propyl, isopropyl, n-butyl, sec.-butyl, iso-butyl, tert.-butyl or phenyl, or R$^1$ and R$^2$ together represent the butadiene-1,4-diyl radical, R$^3$ represents methoxy-, ethoxy-, n- or isopropoxy-, sec.-butoxy-, 2,2-dimethylpropoxy-, 2-methoxyethoxy-, 2-ethoxyethoxy-, 2-methylthioethoxy-, 2-ethylthioethoxy-, 2,2,2-trifluoroethoxy-, cyanomethoxy-, cyanoethoxy-, allyloxy-, methallyloxy-, 2-propynyloxy-, 1,1-dimethyl-2-propynyloxy-, cyclopentyloxy-, cyclohexyloxy- or cyclohexylmethoxy-, or represents the group

in which

R$^4$ represents methyl, ethyl, n- or iso-propyl, 2,2-dimethylpropyl, 2-methoxyethyl, 2-ethoxyethyl, 2-propoxyethyl, 3-methoxypropyl, 3-ethoxypropyl, 3-butoxypropyo, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propynyl, 1,1-dimethyl-2-propynyl, cyclopropyl, cyclobutyl, cyclopentyl or cyclohexyl, R$^5$ represents hydrogen, methyl, ethyl, n- or isopropyl, 2,2-dimethylpropyl, 2-methoxyethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propynyl, 1,1-dimethyl-2-propynyl or cyclohexyl, or R$^4$ and R$^5$ together with the nitrogen atom at which they are located represent pyrrolidine, piperidine, 2-methylpiperidine, 3-methylpiperidine, 4-methylpiperidine, hexahydro-1H-azepine, morpholine, 2,6-dimethylmorpholine, thiazolidine, N$^1$-methylpiperazine or N$^1$-propylpiperazine, R$^6$ represents hydrogen, methyl or chlorine and Q represents sulphur.

4. A substituted 2-phenyl-2,2-difluoroethyllthiolcarbonate according to claim 1, in which R$^1$ represents hydrogen, ethoxycarbonyl, isopropoxycarbonyl, sec.-butoxycarbonyl or cyclopentyloxycarbonyl, R$^2$ represents hydrogen, methyl, isopropyl or phenyl, R$^3$ represents ethoxy, isopropoxy, sec.-butoxy or cyclopentyloxy, or represents the group

in which

R$^4$ represents methyl or methoxyethyl and

R$^5$ represents hydrogen or methyl or

R$^4$ and R$^5$ together represent pentane-1,5-diyl, or represent 3-oxa-pentane-1,5-diyl, R$^6$ represents hydrogen, methyl or chlorine and Q represents sulphur.

5. A substituted 2-phenyl-2,2-difluoroethylthiolcarbonate according to claim 1, in which R$^1$ and R$^2$ together represent the butadiene-1,4-diyl radical, R$^3$ represents ethoxy, isopropoxy, sec.-butoxy or cyclopentyloxy, or represents the group $$-N\begin{matrix}R^4\\R^5\end{matrix}$$

in which

R$^4$ represents methyl or methoxyethyl,

R$^5$ represents hydrogen or methyl, or $R^4$ and $R^5$ together represent pentane-1,5-diyl, or represent 3-oxa-pentane-1,5-diyl, $R^6$ represents hydrogen, methyl or chlorine, and Q represents sulphur.

6. A substituted 2-phenyl-2,2-difluoroethylthiolcarbonate according to claim 1, in which $R^1$ represents hydrogen, ethoxycarbonyl, isopropoxycarbonyl, sec.-butoxycarbonyl or cyclopentyloxycarbonyl, $R^2$ represents hydrogen, methyl, isopropyl or phenyl, $R^3$ represents ethoxy, isopropoxy, sec.-butoxy or cyclopentyloxy, and $R^6$ represents hydrogen or methyl.

7. A compound according to claim 1, wherein such compound is 2,5-bis-(isopropoxycarbonyl)-3-methyl-4-(2-phenyl-2,2-difluoroethylthiocarbonyloxy)-thiophene of the formula

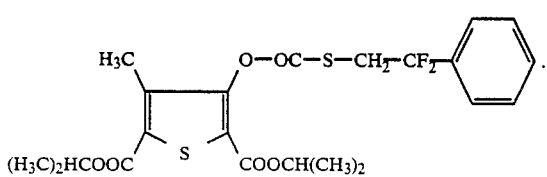

8. A compound according to claim 1, wherein such compound is 2-propoxycarbonyl-3-phenyl-4-(2-phenyl-2,2-difluoroethylthiocarbonyloxy)-5-(N-piperidine-carbonyl)-thiophene of the formula

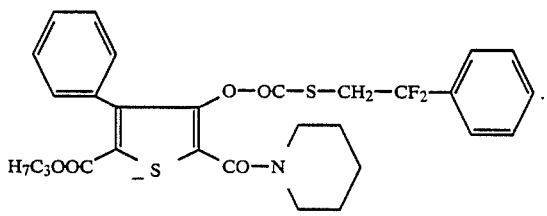

9. A compound according to claim 1, wherein such compound is 2-isopropoxycarbonyl-3-methyl-4-(2-phenyl-2,2-difluoroethylthiocarbonyloxy)-5-(N-morpholinocarbonyl)-thiophene of the formula

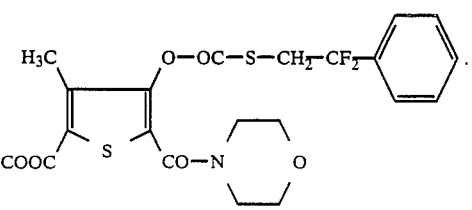

10. A compound according to claim 1, wherein such compound is 2,5-bis-ethoxycarbonyl-3-methyl-4-(2-phenyl-2,2-difluoroethylthiocarbonyloxy)-thiophene of the formula

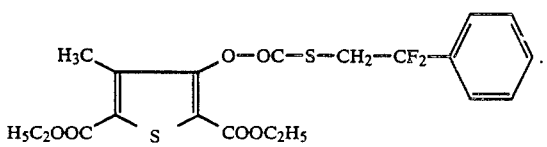

11. A fungicidal composition comprising a fungicidally effective amount of a compound according to claim 1 and a diluent.

12. A method of combating fungi which comprises applying to such fungi or to a fungus habitat a fungicidally effective amount of a compound according to claim 1.

13. The method according to claim 12, wherein such compound is
  2,5-bis-(isopropoxycarbonyl)-3-methyl-4-(2-phenyl-2,2-difluoroethylthiocarbonyloxy)-thiophene,
  2-propoxycarbonyl-3-phenyl-4-(2-phenyl-2,2-difluoroethylthiocarbonyloxy)-5-(N-piperidinecarbonyl)-thiophene,
  2-isopropoxycarbonyl-3-methyl-4-(2-phenyl-2,2-difluoroethylthiocarbonyloxy)-5-(N-morpholinocarbonyl)-thiophene or
  2,5-bis-ethoxycarbonyl-3-methyl-4-(2-phenyl-2,2-difluoroethylthiocarbonyloxy)-thiophene.

* * * * *